United States Patent
Tahara

(10) Patent No.: US 7,592,005 B2
(45) Date of Patent: Sep. 22, 2009

(54) MONOCLONAL ANTIBODY

(75) Inventor: Tomoyuki Tahara, Takasaki (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 141 days.

(21) Appl. No.: 10/451,947

(22) PCT Filed: Dec. 26, 2001

(86) PCT No.: PCT/JP01/11493

§ 371 (c)(1),
(2), (4) Date: Jun. 27, 2003

(87) PCT Pub. No.: WO02/057316

PCT Pub. Date: Jul. 25, 2002

(65) Prior Publication Data
US 2004/0136982 A1 Jul. 15, 2004

(30) Foreign Application Priority Data
Dec. 28, 2000 (JP) .............................. 2000-403245

(51) Int. Cl.
*A61K 39/395* (2006.01)
*C12P 21/08* (2006.01)
*G01N 33/53* (2006.01)

(52) U.S. Cl. ............................ 424/143.1; 530/388.22

(58) Field of Classification Search .............. 424/143.1; 530/388.22
See application file for complete search history.

(56) References Cited

U.S. PATENT DOCUMENTS

2002/0041847 A1 * 4/2002 Goldenberg ................ 424/1.49

FOREIGN PATENT DOCUMENTS

| EP | 19960936 | * | 12/1999 |
| EP | 0 997 152 A1 | | 5/2000 |
| WO | WO/9814580 | * | 4/1998 |
| WO | WO 98/37913 | | 9/1998 |
| WO | WO 99/43703 | | 9/1999 |

OTHER PUBLICATIONS

Ozaki et al. (Tokushima J. Exp. Med. 43:7-15 (1996).*
Ohtomo et al. (Biochem Biophys Res. Commun. 258(3):583-91 (1999)).*
Goto et al. (Blood 84:1922-1930 (1994).*
Kupzig et al. (Traffic 4:694-709 (2003).*
sequence search result (result #15).*
Chari et al. (Cancer Research 52:127-131 (1992).*
Ozaki et al. (Cancer 82:2184-2190 (1998).*
Jain (Scientific American July pp. 58-64 (1994)).*
Chatterjee et al (Cancer Immunol. Imunother., 38:75-82 (1994)).*
Dermer Biotechnology 12: 320 (1994).*
Gura et al (Science 278:1041-1042 (1997)).*
search output from ATCC website for hybridomas: 5-71 (FERM BP-7417), 7-90G (FERM BP-7418), 9-16-1 (FERM BP-7812), and b-76-8 (FERM BP-7822); and for RPMI 8226 (ATCC CCL-155).*
Chabner et al., Cancer Treat. Rep. 62:429-33 (1978)) (Abstract).*
Ozaki et al. (Blood 90(8):3179-3186 (1997)).*
Ozaki et al. (Tokushima J. Exp. Med. 43(1-2):7-15 (1996) (Abstract).*
Ishikawa et al. Genomics 26:527-534 (1995).*
Ohtomo et al. Biochem. Biophys. Res. Comm. 258:583-591 (1999).*
Campbell et al, Biology, 5th ed. p. 856, 1999.*
Wong et al., Oncogenomics 26:1971-1982 (2007).*
Walter-Yohrling et al., Cancer Research 63:8939-8947 (2003).*
Voskoglou-Nomikos et al., Clin. Can. Res. 9:4227-4239 (2003).*
Bruland, Acta. Oncol. 34(8): 1085-94, 1995, (abstract).*
Ross et al., Eur. J. Biochem. 104(2): 381-90, 1980, (abstract).*
Ghose et al., Crit. Rev. Ther. Drug Carrier Syst. 3(4): 263-359, 1987 (abstract ).*
Jatro Jaime et al., "A method for detecting antibody internalization in drug targeting", International Journal of Oncology 17: 835 839, 2000.
Ozaki, K., et al., "Localization and Imaging of Human Plasmacytoma Xenografts in Severe Combined Immunodeficiency Mice by a New Murine Monoclonal Antibody, Anti-HM1.24", The 1$^{st}$ Department of Internal Medicine, School of Medicine, The University of Tokushima, Tokushima 770, Japan (Mar. 25, 1996) (Tokushima J., exp. Med. 43, pp. 7-15).
Abstract, Yasuo Koishihara, et al., JP11092399, Apr. 6, 1999.
International Search Report, Apr. 29, 2004; pp. 1-4 /1b/.
Shuji Ozaki et al., "Radioimmunodetection of Human Myeloma Xenografts with a Monoclonal Antibody Directed against a Plasma Cell Specific Antigen, HM1.24", Cancer, vol. 82, No. 11, (1998), pp. 2184-2190.
Shuji Ozaki et al., "Humanized Anti-HM1.24 Antibody Mediates Myeloma Cell Cytotoxicity That is Enhanced by Cytokine Stimulation of Effector Cells", Blood, vol. 93, No. 11, (1999), pp. 3922-3930.
Shuji Ozaki et al., "Immunotherapy of Multiple Myeloma With a Monoclonal Antibody Directed Against a Plasma Cell-Specific Antigen, HM1.24", Blood, vol. 90, No. 8, (1997), pp. 3179-3186.
Ravi V.J. Chari et al., "Immunoconjugates Containing Novel Maytansinoids: Promising Anticancer Drugs", 6175 Cancer Research, 52(1992), No. 1, pp. 127-131.
Tzu-Chieh Chao et al., "Binding and Internalization of Anti-Sarcoma igG and igM Antibodies", Journal of Surgical Research 70, (1997), pp. 27-33 Article No. JR975084.

* cited by examiner

*Primary Examiner*—David J. Blanchard
*Assistant Examiner*—Lynn Bristol
(74) *Attorney, Agent, or Firm*—Stephen A. Bent; Foley & Lardner LLP

(57) ABSTRACT

A monoclonal antibody or a functional fragment thereof that binds to a human BST2 antigen existing on the cell surface and can be localized through internalization into the cell, a complex comprising the monoclonal antibody or a functional fragment thereof and a therapeutic agent, and a pharmaceutical composition comprising, as an active ingredient, the complex.

4 Claims, 7 Drawing Sheets
(1 of 7 Drawing Sheet(s) Filed in Color)

Reactivity of anti-human BST2 antibody (fluorescence intensity)

Solid line → Anti-human BST2 antibody

Dashed line → Control antibody

Fig. 4

SEQ ID NO: 1

5'-GTGGAATTCATGGCATCTACTTCGTATGACTATTGCAGAGTGCCCATGGAAGACGGGGATAAGCGCTGT

AAGCTTCTGCTGGGGATAGGAATTCTGGTGCTCCTGATCATCGTGATTCTGGGGGTGCCCTTGATTATCTTC

ACCATCAAGGCCAACAGCGAGGCCTGCCGGGACGGCCTTCGGGCAGTGATGGAGTGTCGCAATGTCACCCAT

CTCCTGCAACAAGAGCTGACCGAGGCCCAGAAGGGCTTTCAGGATGTGGAGGCCCAGGCCGCCACCTGCAAC

CACACTGTGATGGCCCTAATGGCTTCCCTGGATGCAGAGAAGGCCCAAGGACAAAAGAAAGTGGAGGAGCTT

GAGGGAGAGATCACTACATTAAACCATAAGCTTCAGGACGCGTCTGCAGAGGTGGAGCGACTGAGAAGAGAA

AACCAGGTCTTAAGCGTGAGAATCGCGGACAAGAAGTACTACCCCAGCTCCCAGGACTCCAGCTCCGCTGCG

GCGCCCCAGCTGCTGATTGTGCTGCTGGGCCTCAGCGCTCTGCTGCAGTGA-3'

Fig. 5

SEQ ID NO: 2

```
              10         20         30         40         50         60
              |          |          |          |          |          |
    MASTSYDYCR VPMEDGDKRC KLLLGIGILV LLIIVILGVP LIIFTIKANS EACRDGLRAV 70         80         90        100        110        120
              |          |          |          |          |          |
    MECRNVTHLL QQELTEAQKG FQDVEAQAAT CNHTVMALMA SLDAEKAQGQ KKVEELEGEI 130        140        150        160        170        180
              |          |          |          |          |          |
    TTLNHKLQDA SAEVERLRRE NQVLSVRIAD KKYYPSSQDS.SSAAAPQLLI VLLGLSALLQ
```

MONOCLONAL ANTIBODY

The application contains at least one drawing executed in color. Copies of this patent or patent application publication with color drawing(s) will be provided by the Office upon request and payment of the necessary fee.

TECHNICAL FIELD

The present invention relates to an antibody that recognizes a human BST2 antigen existing on a cell surface. More particularly, the present invention relates to a monoclonal antibody or a functional fragment thereof that binds to the human BST2 antigen and can be localized through internalization into the cell.

The present invention also relates to a complex that comprises the monoclonal antibody or a functional fragment thereof bound to a therapeutic reagent.

BACKGROUND ART

Cancer (tumor) is the leading cause of death in Japan, and the number of patients has increased every year. Accordingly, development of highly effective and safe agents or therapies is strongly desired. Multiple myeloma, a type of hematopoietic tumor, is an incurable B cell tumor that develops abnormality in the final phase of B cell differentiation. Clinically, the course of multiple myeloma is similar to that of end-stage plasma cell leukemia. It is a neoplasm characterized by accumulation of cloned plasma cells, and it often involves the secretion of an immunoglobulin chain. In bone marrow infiltration caused by the tumor cells, uncontrollable growth of myeloma cells involving various complications such as anemia, hypoglobulinemia, or infection with bacteria is observed. In the case of multiple myeloma, the level of interleukin 6 (IL6) is elevated and then the osteoclast is enlarged, which induces bone pain, bone fracture, and hypocalcemia. High-level myeloma immunoglobulin and hypocalcemia often involve kidney failure.

Up to the present, various therapies have been attempted on multiple myeloma patients, although clinical effects on patients as a whole are still low. Multidrug therapy using melphalan and prednisolone is a standard chemotherapeutic regimen. This therapy is intermittently continued for approximately 2 years, and the symptoms go into remission. However, relapses are still observed and the patient dies (Alexanian et al., New England J Medicine, 1994, Vol. 330: 484). These agents exhibit toxicity to normal cells instead of acting specifically on tumor cells alone. Thus, serious side effects develop, and therapeutic effects are limited. Since the 1980s, ultra high-dose chemotherapy with hematopoietic stem cell transplantation has been still actively investigated, although its clinical effect remains low.

In order to reduce toxicity to normal cells, the use of a targeting antibody conjugated with a radionuclide or other cytotoxic substances has been attempted (Goldenberg, Semin Nucl Med., 1989, Vol. 19: 332). However, the ratio of the targeting antibody to be incorporated into the tumor cell is generally low. It is no more than 0.01% to 0.001% of the total amount injected (Vaughan et al., Brit. J Radiol., 1987, Vol. 60: 567). The development of an antibody that can be rapidly localized (internalized) in the target cell can improve the effectiveness of the therapy and reduce the side effects thereof. This can be realized because such an antibody binds to chemically synthetic toxins or therapeutic reagents such as anticancer agents or radionuclides, thereby rapidly emitting these cytotoxic substances in the cells.

Antibody therapies targeting multiple myeloma have been heretofore attempted. IL-6 has been considered to be a major growth factor for multiple myeloma cells (Kawano et al., Nature, 1988, Vol. 332: 83; Klein et al., Blood, 1991, Vol. 73: 517). Accordingly, therapies have been attempted on multiple myeloma patients using a neutralizing antibody against IL-6 or IL-6 receptor for the purpose of blocking the IL-6 signal transduction system. Although the proliferation of multiple myeloma cells was inhibited in patients who had experienced changes of the disease to leukemia, tumors recurred and clinical effectiveness has not yet attained (Bataille et al., Blood, 1995, Vol. 86: 68; Van Zaanen et al., Br J Haematol., 1998, Vol. 102: 783; the Journal of the Japan Society for Clinical Immunology, 1997, Vol. 20: 87). Further, myeloma cell-expressing antigens such as CD19 (Grossbard et al., Br J Haematol., 1998, Vol. 102: 509), CD20 (Hussein et al., Blood, 1999, Vol. 94 [Suppl.1]: 313), CD38 (Maloney et al., Semin Hematol., 1999, Vol. 36 [Suppl.3]: 30), CD54 (Huang et al., Cancer Res., 1995, Vol. 55: 610), CD138 (Wijdenes et al., Br J Haematol., 1996, Vol. 94: 318), or Muc-1 (Treon et al., Blood, 1999, Vol. 93: 1287) have been reported as candidates for the target antigens for the antibody therapy, although none thereof has yet been put to practical use.

Recently, the bone marrow stromal antigen 2 ("BST2," which may be referred to as "HM1.24 antigen") has been reported as an antigen that is expressed at high level in the myeloma cells (Goto et al., Blood, 1994, Vol. 84: 1922; Ohtomo et al., Biochem Biophys Res Commun., 1999, Vol. 258: 583). BST2 is a type II transmembrane glycoprotein having a molecular weight of approximately 30 kDa and comprising 180 amino acid residues. A homodimer is formed by S—S bond and expressed on a cytoplasmic membrane. A BST2 protein is not expressed in, for example, a normal peripheral blood cell, bone marrow cell, reactive lymphocyte, liver, kidney, or heart, although it is highly specifically expressed in the plasma cell and in the myeloma cell. Detailed biological activities are not yet known, although BST2 is considered to be associated with terminal B cell differentiation (Ishikawa et al., Genomics, 1995, Vol. 26: 527). Regarding an antibody against human BST2, a mouse monoclonal antibody, which was prepared by immunizing a nonhuman mammalian animal such as a mouse with a human BST2 expressing cell line, has been reported (Goto et al., Blood, 1994, Vol. 84: 1922). Also reported is a chimeric antibody that comprises a variable region of this mouse monoclonal antibody and a constant region of human immunoglobulin (Ozaki et al., Blood, 1999, Vol. 93: 3922). When this antibody was administered ten days after the injection of the myeloma cells to a human myeloma cells-transplanted SCID mouse, tumor growth was inhibited (Ozaki et al., Blood, 1997, Vol. 90: 3179). The antibody therapy for multiple myeloma that utilizes BST2 as a target antigen is expected to be promising. Since the expression of BST2 is reported in other lymphoid tumors as well as in myeloma, the anti-BST2 antibody therapy could be effective on those tumors. These antibodies, however, do not have activity generating BST2 modulation by their binding (Ozaki et al., Ketsueki, Shuyouka (Blood, Tumors), 2000, Vol. 41: 128), and any anti-BST2 antibody that induces rapid internalization, from which enhanced effectiveness of chemotherapeutants or therapeutic reagents such as radionuclides and reduced side effects can be expected, has not yet been reported at all. In general, it is known that an antibody that binds to an antigen protein expressed on the cell surface and induces internalization into the cells can be obtained. It is not always clear whether or not such an antibody can be obtained regarding all the cell surface antigens.

DISCLOSURE OF THE INVENTION

An object of the present invention is to provide a therapeutic agent based on a novel mechanism for treating currently obstinate diseases such as multiple myeloma by developing an antibody that can bind to human BST2 and can induce localization (internalization) into the human BST2-expressing cells such as tumor cells.

The present inventors have conducted concentrates studies in order to produce an antibody against human BST2. As a result, they have succeeded in obtaining an anti-BST2 antibody that can be rapidly internalized in the target cell. This has led to the completion of the present invention. The present invention includes the following inventions.

(1) A monoclonal antibody or a functional fragment thereof, which binds to a human BST2 antigen existing on a cell surface and can be localized through internalization into the cell.

(2) The monoclonal antibody or a functional fragment thereof according to (1), wherein the cell is the RPMI 8226 strain (ATCC CCL-155), the monoclonal antibody binds thereto under ice cooling, internalization proceeds within 120 minutes after the initiation of culture at 37° C., and the average fluorescence intensity of the fluorescent substance, which represents the amount of a complex of human BST2/the monoclonal antibody existing on the cell surface, is 50% or less compared with that at the initiation of culture.

(3) The monoclonal antibody or a functional fragment thereof according to (1), wherein the cell is the RPMI 8226 strain, the monoclonal antibody binds thereto under ice cooling, internalization proceeds within 90 minutes after the initiation of culture at 37° C., and the average fluorescence intensity of the fluorescent substance, which represents the amount of a complex of human BST2/the monoclonal antibody existing on the cell surface, is 50% or less compared with that at the initiation of culture.

(4) The monoclonal antibody or a functional fragment thereof according to (1), wherein the cell is the RPMI 8226 strain, the monoclonal antibody binds thereto under ice cooling, internalization proceeds within 60 minutes after the initiation of culture at 37° C., and the average fluorescence intensity of the fluorescent substance, which represents the amount of a complex of human BST2/the monoclonal antibody existing on the cell surface, is 50% or less compared with that at the initiation of culture.

(5) The monoclonal antibody or a functional fragment thereof according to (1), wherein the cell is the RPMI 8226 strain, the monoclonal antibody binds thereto under ice cooling, internalization proceeds within 30 minutes after the initiation of culture at 37° C., and the average fluorescence intensity of the fluorescent substance, which represents the amount of a complex of human BST2/the monoclonal antibody existing on the cell surface, is 50% or less compared with that at the initiation of culture.

(6) The monoclonal antibody or a functional fragment thereof according to (1), wherein the cell is the RPMI 8226 strain, the monoclonal antibody binds thereto under ice cooling, internalization proceeds within 15 minutes after the initiation of culture at 37° C., and the average fluorescence intensity of the fluorescent substance, which represents the amount of a complex of human BST2/the monoclonal antibody existing on the cell surface, is 50% or less compared with that at the initiation of culture.

(7) The monoclonal antibody or a functional fragment thereof according to (1), which recognizes an epitope in the amino acid sequence of amino acid number of 50 to 180 as shown in SEQ ID NO: 2.

(8) The monoclonal antibody or a functional fragment thereof according to (1), which is IgG1(κ) or IgG4(κ).

(9) The monoclonal antibody or a functional fragment thereof according to (1), which is a human antibody.

(10) The monoclonal antibody or a functional fragment thereof according to (1), which is produced from a hybridoma under the accession numbers FERM BP-7417, FERM BP-7418, FERM BP-7821, or FERM BP-7822 (5-7I, 7-90G, 9-16-1, or b-76-8, respectively).

(11) The monoclonal antibody or a functional fragment thereof according to (1), which is obtained by cloning a human antibody gene from a hybridoma under the accession numbers FERM BP-7417, FERM BP-7418, FERM BP-7821, or FERM BP-7822 (5-7I, 7-90G, 9-16-1, or b-76-8, respectively), introducing the gene into a host cell in an expressible state, and culturing the host cell.

(12) A complex comprising the monoclonal antibody or a functional fragment thereof according to any one of (1) to (11) bound to a therapeutic agent.

(13) The complex according to (12), wherein the therapeutic agent is at least one member selected from the group consisting of radionuclides, bacterial toxins, chemotherapeutants, and prodrugs.

(14) A pharmaceutical composition targeting a human BST2-expressing cell, which comprises, as an active ingredient, the complex according to (12) or (13).

(15) The pharmaceutical composition according to (14), which is applied to lymphocytic tumor, rheumatism, or primary localized cancer.

(16) The pharmaceutical composition according to (14), which is applied to multiple myeloma.

(17) A process for producing the monoclonal antibody or a functional fragment thereof according to (1), wherein hybridomas are prepared through fusion between a spleen cell of a nonhuman animal immunized with a polypeptide comprising at least a partial amino acid sequence of the human BST2 antigen, and a myeloma cell, a hybridoma that produces an antibody bound to the human BST2 antigen is selected from among the hybridomas, an antibody that binds to the human BST2 antigen produced from the selected hybridoma is allowed to react with a human BST2 antigen-expressing cell, and selection is performed employing, as an indication, a decrease in the amount of a complex of the human BST2/the antibody on the cell surface in the process of the cell culture.

The present invention also provides a process for introducing a biologically active substance into a human BST2-expressing cells by binding the biologically active substance to the monoclonal antibody or a functional fragment thereof according to any of (1) to (11) above chemically or by genetic engineering. The term "biologically active substance" refers to a substance that can cause some biological changes to the cell into which the substance was introduced. Examples of biological changes include (i) acceleration or inhibition of the cell growth, (ii) acceleration or inhibition of differentiation or dedifferentiation, (iii) changes in actions such as signal transduction from a cell to another cell, and (iv) cell death. Specific examples thereof include: chemotherapeutants; radionuclides; bacterial toxins; various cytokines; enzymes associated with synthesis or decomposition of hormones, transcripts, or sugar chains; and DNA or RNA having the aforementioned functions to the cell.

Terms used herein are defined as below.

"Human BST2" is an abbreviation of bone marrow stromal antigen 2, which is a type II transmembrane glycoprotein having a molecular weight of approximately 30 kDa and consisting of 180 amino acid residues, forms a homodimer by disulfide bond, and is specifically expressed on the cytoplasmic membrane such as plasma cells or myeloma cells (for example, Goto et al., as above, Ohtomo et al., as above).

"Internalization" or "rapid internalization" refers to a phenomenon in which an antibody forms an immune complex with a cell surface antigen and is incorporated into the cell within a short period of time instead of nonspecific pinocytosis of the cell as one of the mechanisms that are generally referred to as endocytosis. For example, when an antibody is generally incorporated based on this mechanism, an immune complex of an antibody and a receptor migrates on the cell surface in an energy-dependent manner after binding, is concentrated (capped) at one point, and is then incorporated in the cell within 1 to several minutes, and within 12 hours at the longest, although it varies depending on reaction conditions, properties of antibody or antigen, or the like. An antibody that binds to the antigen existing on a cell surface and that is incorporated through internalization in the cell may be referred to as "an antibody that can induce internalization" herein.

The sentence "the average fluorescence intensity of fluorescent substance, which represents the amount of a complex of human BST2/monoclonal antibody on a cell surface, is 50% or less compared with that at the initiation of culture" refers to a phenomenon that occurs when culturing a cell having human BST2 antigen on its surface in the presence of anti-BST2 antibody. That is, the ratio of complexes remaining after a given period of time is 50% or less relative to 100, i.e., the amount of an existing complex of human BST2/monoclonal antibody formed by the immunological reaction with human BST2 on the cell surface at the initiation of culture. In other words, 50% or more anti-BST2 antibodies forming an immunological complex were incorporated through internalization into the cell.

A "prodrug" refers to a precursor agent that is converted to an active agent by the functions of endogenous enzymes or the like when administered to an organism.

A "chemotherapeutant" refers to an agent that selectively acts on a pathogen and cures diseases resulting from tumors, etc. without imparting significant damages to patients.

Each of the alphabetic characters that is used to represent an amino acid in this specification or these drawings refers to one of the following amino acids:

(G) glycine, (A) alanine, (V) valine, (L) leucine, (I) isoleucine, (S) serine, (T) threonine, (D) aspartic acid, (E) glutamic acid, (N) asparagine, (Q) glutamine, (K) lysine, (R) arginine, (C) cysteine, (M) methionine, (F) phenylalanine, (Y) tyrosine, (W) tryptophan, (H) histidine, (P) proline. Each of the alphabetic characters that is used to represent DNA is as follows: (A) adenine, (C) cytosine, (G) guanine, (T) thymine.

The present invention is hereafter described in detail.

Human BST2 can be produced by a suitable process that is known in the art such as chemical synthesis or cell culture in addition to genetic recombination technique based on known nucleotide sequences or amino acid sequences (SEQ ID NO: 1 or 2, respectively). A partial sequence of human BST2 can be produced by genetic recombination technique or chemical synthesis in accordance with the process known in the art that is described later. Alternatively, it can be produced by suitably cleaving human BST2 using a protease or the like.

The antibody according to the present invention includes various anti-human BST2 monoclonal antibodies that can induce internalization. Examples of the antibodies include the anti-human BST2 monoclonal antibody as described in Examples 7 to 15; and a monoclonal antibody comprising a heavy chain and/or light chain having an amino acid sequence comprising deletion, substitution, or addition of one or several amino acids in each of the heavy chain and/or light chain amino acid sequences constituting the antibody that can induce internalization. The aforementioned partial modification (deletion, substitution, insertion, or addition) of amino acids can be introduced in the amino acid sequence of the antibody according to the present invention by partially modifying a nucleotide sequence that encodes the amino acid sequence. Partial modification of this nucleotide sequence can be introduced by a conventional process using known site-specific mutagenesis (Proc Natl Acsd Sci USA, 1984, Vol. 81: 5662; Sambrook et al., Molecular Cloning A Laboratory Manual (1989) Second edition, Cold Spring Harbor Laboratory Press). The antibody of the present invention includes antibodies having any immunoglobulin class or subclass. Preferably, an antibody has a human immunoglobulin class and a subclass. A preferable class and a subclass are immunoglobulin G(IgG), and IgG1 and IgG4 are particularly preferable. A preferable light chain is κ.

A preferable example of the antibody or a fragment thereof according to the present invention is as follows. After the antibody or a fragment thereof binds to the myeloma cell strain RPMI 8226 (ATCC CCL-155) under ice cooling, internalization proceeds within approximately 120 minutes, preferably approximately 90 minutes, further preferably approximately 60 minutes, particularly preferably approximately 30 minutes, and still more preferably approximately 15 minutes after the initiation of culture at 37° C. As a result, the average fluorescence intensity of the fluorescent substance, which represents the amount of a complex of human BST2/anti-BST2 antibody on the cell surface, is 50% or less compared with that at the initiation of culture.

Another preferable example of the antibody or a fragment thereof according to the present invention is a monoclonal antibody or a sequence consisting of fragment thereof that recognizes an epitope constituted by at least 8 continuous or discontinuous amino acid residues in the human BST2 amino acid sequence (SEQ ID NO: 2), and that has the property to induce internalization. An example thereof is a monoclonal antibody or a fragment thereof that recognizes an epitope in amino acid sequence of the amino acid number of 10 to 180, 20 to 180, 30 to 180, 40 to 180, 50 to 180, 50 to 170, 50 to 160, 50 to 150, 50 to 140, 50 to 130, 50 to 120, 50 to 110, 50 to 100, 50 to 90, 50 to 80, 50 to 70, and 50 to 60 as shown in SEQ ID NO: 2 and that can induce internalization.

A further preferable example of the antibody or a fragment thereof according to the present invention is an antibody having cross-reactivity with human BST2 and monkey BST2. Such an antibody is presumed to recognize an epitope structure that is identical or very similar between human BST2 and monkey BST2. Thus, this is advantageous since various tests can be previously made by using monkeys as experimental animals before conducting clinical tests on humans. Specific examples of such an antibody are those prepared from hybridoma 9-16-1 (FERM BP-7821) or hybridoma b-76-8 (FERM BP-7822).

A fragment of the antibody according to the present invention refers to a part of the antibody as defined above. Specific examples thereof include F(ab')2, Fab', Fab, Fv, disulphide-linked FV, Single-Chain FV (scFV), and a polymer thereof (D. J. King., Applications and Engineering of Monoclonal Antibodies, 1998, T. J. International Ltd.). Such a fragment of the antibody can be obtained by conventional techniques, for example, digestion of antibody molecules by protease such as papain or pepsin, or by known techniques of genetic engineering. The term "functional fragment" refers to an antibody fragment that specifically binds to an antigen to which the antibody specifically binds.

The antibody according to the present invention can be produced by, for example, the following process. Specifically, a nonhuman mammalian animal such as a mouse, rabbit, goat, or horse is immunized with human BST2 or a part thereof as defined above, a binding product thereof with a suitable substance for enhancing antigenicity of the antigen (e.g., bovine serum albumin), or a cell having a large amount of human BST2 expressed on its surface together with an immunopotentiating agent (e.g., Freund's Adjuvant), if necessary. Alternatively, an expression vector in which BST2 has been introduced can be administered to nonhuman mammalian animals for immunization. A monoclonal antibody is produced by preparing a hybridoma from an antibody-producing cell obtained from the immunized animal and a myeloma cell incapable of producing an autoantibody, cloning the hybridoma, selecting a clone that produces a monoclonal antibody having specific affinity to the antigen used for immunization, and selecting a clone capable of inducing internalization by the process described below. More preferably, the antibody according to the present invention may be a human antibody, by using a nonhuman animal that retains a non-rearranged human antibody gene and produces a human antibody specific to the antigen by immunization. The term "human antibody" refers to an antibody or a functional fragment thereof that is an expression product of a human-derived antibody gene.

More specifically, the antibody according to the present invention can be produced in the following manner. A hybridoma that secretes the monoclonal antibody can be produced by the process according to Köhler and Milstein (Nature, 1975, Vol. 256, 495-497) or a process in accordance therewith. Specifically, the hybridoma is produced through the cell fusion between an antibody-producing cell contained in the spleen, lymph node, bone marrow, tonsilla, or the like that is obtained from the thus immunized animal, and preferably in the lymph node or spleen, and, preferably, a myeloma cell incapable of producing autoantibodies derived from a mammalian animal such as a mouse, rat, guinea pig, hamster, rabbit, or human. Cell fusion can be generally performed by, for example, mixing the antibody-producing cell with the myeloma cell in a highly concentrated polymer solution such as polyethylene glycol (e.g., with a molecular weight of 1500 to 6000) at approximately 30 to 40° C. for approximately 1 to 10 minutes. A hybridoma clone that produces a monoclonal antibody can be screened for by culturing the hybridomas in, for example, a microtiter plate, and assaying the reactivity to the immunogen in the culture supernatant in the well where cell growth is observed, for example, by enzyme immunoassay such as ELISA or immunological processes such as radioimmunoassay or a fluorescent antibody technique.

A monoclonal antibody can be produced from a hybridoma by culturing a hybridoma in vitro and isolating it from the culture supernatant. Alternatively, a hybridoma can be cultured in vivo, for example, in the ascites fluid of a mouse, rat, guinea pig, hamster, or rabbit and a monoclonal antibody can be and isolated from the ascites fluid.

A gene encoding a monoclonal antibody is cloned from an antibody-producing cell such as a hybridoma, incorporated into a suitable vector, and then the vector is introduced into a host (for example, a mammalian cell line such as a Chinese hamster ovary (CHO) cell, E. coli, yeast cell, insect cell, or plant cell) to prepare a recombinant antibody by genetic recombination technique (P. J. Delves, ANTIBODY PRODUCTION ESSENTIAL TECHNIQUES, 1997, WILEY, P. Shepherd and C. Dean, Monoclonal Antibodies, 2000, OXFORD UNIVERSITY PRESS, J. W. Goding, Monoclonal Antibodies: principles and practice, 1993, ACADEMIC PRESS). Further, a technique of preparing transgenic animals is employed in order to prepare a transgenic bovine, goat, sheep, or pig comprising the antibody gene of interest incorporated in the endogenous gene. From the milk of the transgenic animal, a large quantity of antibody gene-derived monoclonal antibodies can also be obtained. When culturing hybridomas in vitro, hybridomas are grown, maintained, and stored using known nutrient media that are used to produce a monoclonal antibody in the culture supernatant or various nutrient media induced and prepared based on known basal media in accordance with various conditions such as properties of the cell strain to be cultured, the purpose of tests and research, or the culture process.

The produced monoclonal antibody can be purified by suitably combining known processes in the art, for example, chromatography by protein A column, ion exchange chromatography, hydrophobic chromatography, salting out with ammonia sulfate, gel filtration, or affinity chromatography.

The monoclonal antibody or a fragment thereof according to the present invention prepared in the above process can form a complex that can be used for missile therapy, etc. by conjugating it to a therapeutic agent. Examples of therapeutic agents to be bound to the antibody include, but are not limited to, the following: radionuclides such as iodine ($^{131}$Iodine: $^{131}$I, $^{125}$Iodine $^{125}$I), yttrium ($^{90}$Yttrium:$^{90}$Y), indium ($^{111}$Indium:$^{111}$In), and technetium ($^{99m}$Technetium:$^{99m}$Tc) (J. W. Goding, Monoclonal Antibodies: principles and practice, 1993, ACADEMIC PRESS); bacterial toxins such as Pseudomonas exotoxin, diphtheria toxin, and ricin; and chemotherapeutants such as methotrexate, mitomycin, and calicheamicin (D. J. King., Applications and Engineering of Monoclonal Antibodies, 1998, T. J. International Ltd, M. L. Grossbard, Monoclonal Antibody-Based Therapy of Cancer, 1998, Marcel Dekker Inc). An example of a more preferable agent is maytansinoid, which can be made into a prodrug by binding to an antibody (Chari et al., Cancer Res., 1992, Vol. 52: 127, Liu et al., Proc Natl Acad Sci USA, 1996, Vol. 93: 8681). An antibody and a therapeutic agent may be bound covalently or non-covalently (e.g., by an ionic bond). For example, a reactive group (e.g., an amino, carboxyl, or hydroxy group) or a coordination group in the antibody molecule is used. If necessary, it is bound to a more reactive group or converted into a reactive group, and a therapeutic agent having a functional group that can bind by reacting with the reactive group (in the case of bacterial toxins and chemotherapeutants) or an ionic group that can form a complex with a coordinating group (in the case of radionuclide) is brought into contact with an antibody to produce the complex according to the present invention. Alternatively, the biotin-avidin system can also be used in the formation of a complex. Further, when a therapeutic agent is a protein or peptide, it can be produced as a fusion protein between the antibody and the protein or peptide by genetic engineering.

More specifically, a maytansinoid-antibody conjugate can be prepared in the following manner (Chari et al., Cancer Res., 1992, Vol. 52: 127, U.S. Pat. No. 5,208,020). Maytansine or ansamitocin P-3 is reduced with the aid of lithium aluminum hydride to prepare maytansinol. The prepared maytansinol was esterified with N-methyl-N-(methyl dithiopropanoyl)-L-alanine in the presence of dichlorohexyl carbodiimide and zinc chloride, and then purified with silica gel chromatography, etc., to prepare a maytansine derivative (May-SS-Me). The antibody is allowed to react with N-succinimidyl-3-(2-pyridylthio)propionic acid, etc. or succinimidyl-4-(N-maleimidemethyl)cyclohexane-1-carboxylic acid, etc. to introduce a dithiopyridyl or maleimide group into the antibody. May-SH that was prepared by reducing May-SS- Me with dithiothreitol or the like is allowed to react with an antibody into which a dithiopyridyl or maleimide group has been introduced. Thus, a maytansinoid-antibody conjugate can be prepared.

The anti-human BST2 antibody according to the present invention or a pharmaceutical composition comprising an anti-human BST2 antibody that was bound to the aforementioned therapeutic agent is included in the scope of the present invention. This composition should comprise a therapeutically effective amount of therapeutic agent, and is formulated in various forms such as oral or parenteral administration. The "therapeutically effective amount" refers to an amount that imparts therapeutic effects regarding given symptoms or dosage regimen. The composition according to the present invention can comprise, in addition to the antibody, one or several members selected from physiologically acceptable additives for formulation, for example, a diluent, preservative, solubilizing agent, emulsifying agent, adjuvant, anti-oxidant, isotonizing agent, excipient, or carrier. Alternatively, it can be mixed with another antibody or another agent such as an antibiotic. A suitable carrier comprises, but is not limited to, physiological saline, phosphate-buffered physiological saline, phosphate-buffered physiological saline glucose liquid, and buffered physiological saline. Further, stabilizers or an agent to prevent adsorption on surfaces for amino acid, sugar, surfactant, or the like that are known in the art may be contained. As a dosage form, a preparation such as a freeze-dried preparation (this form can be used by recomposing by adding a buffered aqueous solution as mentioned above), sustained release preparation, enteric coated preparation, injection, or drop can be selected in accordance with the purpose and design of therapy.

Possible routes of administration are: oral administration; intravenous, intramuscular, hypodermic, or intraperitoneal injection; and non-enteral administration including drug distribution. An optimal administration path is selected based on animal-based experiments. Alternatively, the composition according to the present invention can be directly brought into contact with the lesion of the patient. The dose is suitably determined based on the animal-based experiment or clinical test. For example, the condition or severity, age, body weight, or sex of the patient should be generally taken into consideration.

The antibody or pharmaceutical composition according to the present invention can be applied to the treatment or prevention of various diseases or symptoms that can result from the BST2-expressing cells. Examples of the diseases or symptoms include lymphocytic tumors such as multiple myeloma and rheumatism. In the case of rheumatism, the pharmaceutical composition according to the present invention is allowed to selectively act on an autoantibody-producing cell, i.e., a BST2-expressing plasma cell (plasma B cell). The human monoclonal antibody according to the present invention can be applied to the life extension of a patient having primary localized cancer.

BRIEF DESCRIPTION OF THE DRAWINGS

FIG. 4 is a diagram showing a nucleotide sequence of the full length human BST2 DNA.

FIG. 5 is a diagram showing an amino acid sequence of the full length human BST2.

BEST MODES FOR CARRYING OUT THE INVENTION

Figure 1:
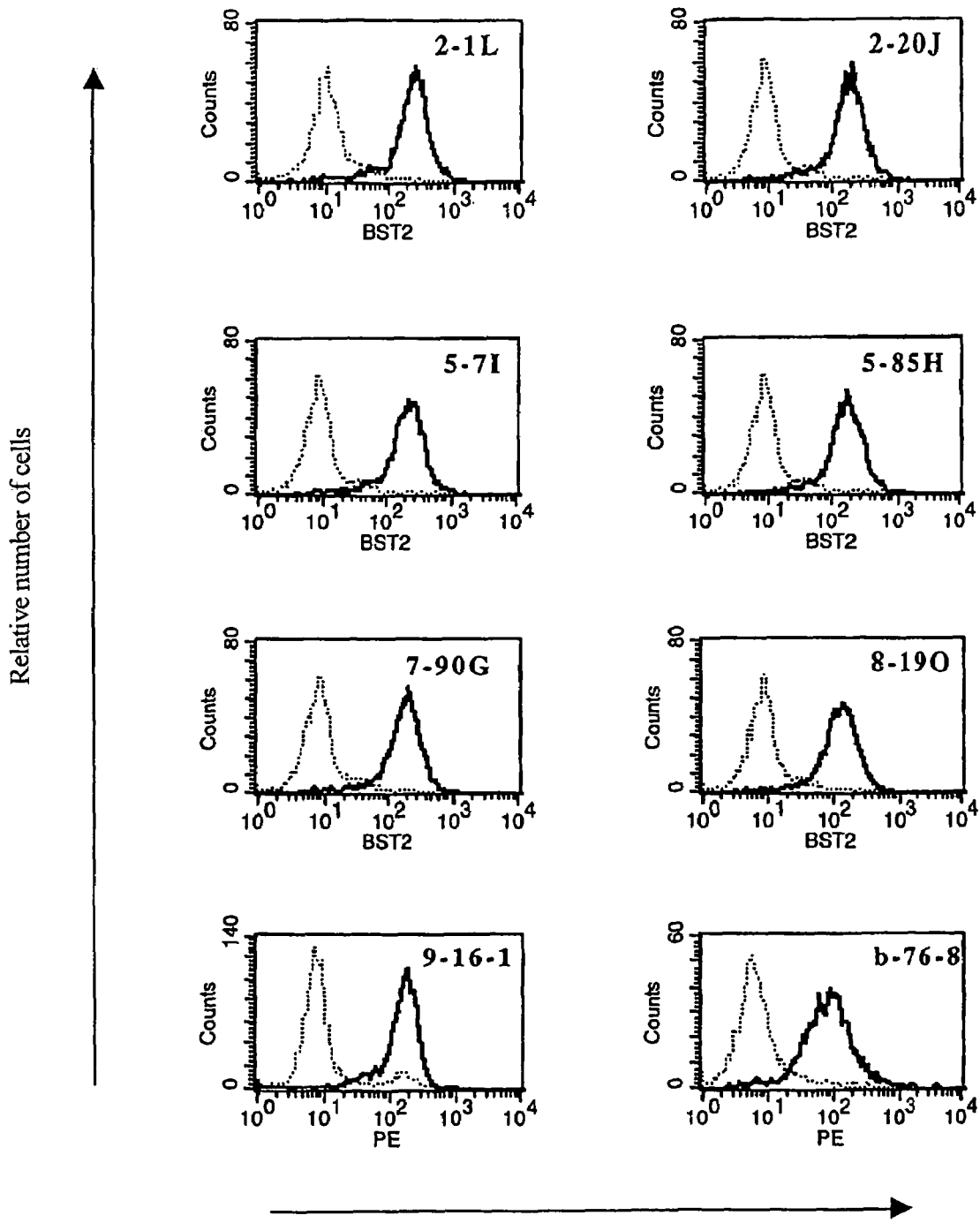
FIG. 1 is a diagram showing reactivity of an anti-human BST2 antibody against the RPMI 8226 cell strain.

The present invention is hereafter described in more detail with reference to the following examples, although the technical scope of the present invention is not limited to embodiments described in the Examples.

EXAMPLE 1

Preparation of Human BST2 Expression Vector

The full length human BST2 DNA (SEQ ID NO: 1) was modified by the polymerase chain reaction (PCR) in order to add the NotI sequence to its 5'-terminus and XbaI and a termination codon to its 3'-terminus. Using the primers 5'-AAGGAAAAAAGCGGCCGCGTGGAAT-TCATGGCATCTAC-3' (SEQ ID NO: 3) and 5'-CTAGTCTAGATCATCACTGCAGCA-GAGCGCTGAGG-3' (SEQ ID NO: 4) and using KOD-Plus (Toyobo Co., Ltd.) as a DNA polymerase and using, as a template, about 20 ng of cDNA synthesized from human bone marrow-derived PolyA+RNA (Clontech) using SuperScript II (Gibco BRL), PCR was carried out for 30 PCR cycles of 94° C. for 15 seconds, 50° C. for 30 seconds, and 68° C. for 1 minute. The modified BST2 sequence was isolated as a NotI-XbaI fragment and then ligated to the pTracer-CMV vector (Invitrogen) that was cleaved with the same enzyme. The resulting plasmid was designated as pTracer-CMV/hBST2.

EXAMPLE 2

Preparation of Soluble Human BST2 Expression Vector

A soluble BST2 protein was prepared in the following manner in an expression system using a baculovirus. Two types of soluble BST2 expression plasmids were prepared. One type had FLAG added to its N-terminus (N-terminus-DYKDDDDK-C terminus (SEQ ID NO: 10), Brizzard et al., Biotechniques (1994) 16:730) (FLAG-sBST2), and another type had FLAG added to its N-terminus and glutathione-S-transferase added to its C-terminus (GST, Smith et al., Gene (1988) 67: 31) (FLAG-sBST2-GST) of the BST2 partial peptide having 54 to 180 amino acid sequences (amino acids 54 to 180 in SEQ ID NO: 2). In order to add a secretion signal sequence and a FLAG codon to the 5'-terminus of the FLAG-sBST2 vector, cDNA of the following DNA sequence: 5'-AG-ATCTATGAAATTCTTAGTCAACGTTGC-CCTTGTTTTTATGGTCGTATACATTTCT TACATCTATGCGGATCGAGACTACAAG-GATGACGATGACAAGGGATCC-3' (SEQ ID NO: 5) comprising a 5'-terminal BglII sequence and a 3'-terminal BamHI sequence was synthesized (Signal-Flag fragment). In order to add the NotI sequence to the 5'-terminal BamHI sequence, the sBST2 domain, the termination codon, and the 3'-terminus, primers 5'-CGAGGATCCCATATGCGGGACGGCCT-TCGGGC-3' (SEQ ID NO: 6) and 5'-AAGGAAAAAAGCG-GCCGCTCACTGCAGCAGAGCGCTGAGG-3' (SEQ ID NO: 7) were used for modification by PCR. PCR was carried out for 35 PCR cycles of 94° C. for 30 seconds, 56° C. for 30 seconds, and 72° C. for 1 minute using Ex-Taq Polymerase (Takara Shuzo Co., Ltd.) and about 20 ng of human spleen-derived 1st strand DNA (Clontech). The modified BST2 sequence was isolated as the BamHI-NotI fragment. The Signal-Flag fragment and the BamHI-NotI fragment were ligated to the pFastBac1 vector (GIBCO) that was cleaved with BglII and NotI enzymes. The resulting plasmid was designated as pFastBac1/FBST2.

Similarly, FLAG-sBST2-GST was modified by PCR using primers 5'-CGAGGATCCCATATGCGGGACGGCCT-TCGGGC-3' (SEQ ID NO: 6) and 5'-AAGGAAAAAAGCG-GCCGCCTGCAGCAGAGCGCTGAGG-3' (SEQ ID NO: 7) in order to add the BamHI sequence to the 5'-terminus and the NotI sequence to the 3'-terminus. PCR was carried out for 30 PCR cycles of 94° C. for 30 seconds, 56° C. for 30 seconds, and 72° C. for 1 minute using Ex-Taq Polymerase (Takara Shuzo Co., Ltd.) and 20 ng of pFastBac1/FBST2. The modified BST2 sequence was isolated as the BamHI-NotI fragment. In order to add GST and the termination codon sequence, modification by PCR was carried out using primers 5'-AAGGAAAAAAGCGGCCGCGCTGGAAGT-TCTGTTCCAGGGGCCCATGTCCCCTATACT AGGT-TATTGG-3' (SEQ ID NO: 8) and 5'-CGGGGTACCT-CAATCCGATTTTGGAGGATGGTCGCC-3' (SEQ ID NO: 9) to add the NotI sequence to the 5'-terminus and the KpnI sequence to the 3'-terminus. PCR was carried out for 30 PCR cycles of 94° C. for 30 seconds, 56° C. for 30 seconds, and 72° C. for 1 minute using Ex-Taq Polymerase (Takara Shuzo Co., Ltd.) and 20 ng of pGEX plasmid (Amersham Pharmacia Biotech). The modified GST sequence was isolated as the NotI-KpnI fragment, and the aforementioned BamHI-NotI fragment and the NotI-KpnI fragment were ligated to the pFast Bac1/FBST2 vector that was cleaved with BamHI-KpnI. The resulting plasmid was designated as pFastBac1/FBST2/GST.

EXAMPLE 3

Preparation of Recombinant Expression Virus

A recombinant virus was prepared using the expression vector prepared in Example 2 and the BAC-TO-BAC Baculovirus Expression System (Gibco BRL) in accordance with the process described in the instructions. The resultant recombinant baculovirus was amplified by adding 0.3 ml of the recombinant baculovirus-containing supernatant to 5 ml of $3 \times 10^6$ Sf9 cells (Invitrogen), culturing the resultant in a flask (T-Flask 25 cm$^2$, CORNING) for four days at 27° C., and collecting the culture supernatant. The same procedure was repeated until the intended amount of viruses was obtained.

EXAMPLE 4

Expression of Soluble Human BST2

A large amount of soluble BST2 was expressed by adding the 80 ml of viruses prepared in Example 3 to 800 ml of HIFIVE™ cells ($1 \times 10^6$/ml, Invitrogen), culturing the resultant at 27° C. for 60 hours, and collecting the culture supernatant. The collected supernatant was centrifuged and filtered through a 0.2 μm PES filter (CORNING), thereby removing waste such as cells.

EXAMPLE 5

Purification of Soluble Human BST2

The soluble BST2s (FLAG-sBST2, FLAG-sBST2-GST) prepared in Example 4 were purified from the culture supernatant in the following manner. A soluble BST2-containing culture supernatant was subjected to affinity purification using the FLAG M2 Affinity Column (SIGMA) in accordance with the attached instructions. PBS(−) was used as an adsorption buffer, and 0.1M glycine-hydrochloride buffer (pH 3) was used as an elution buffer. An elution fraction was adjusted at around pH 7.2 with the addition of 1M Tris-HCl (pH 8.0). The prepared antibody solution was converted into PBS(−) using a dialysis membrane (molecular weight cut off: 10,000, Spectrum Laboratories) and filter-sterilized with a membrane filter MILLEX-GV (pore diameter: 0.22 μm, MILLIPORE). Thus, single-band purified FLAG-sBST2 and FLAG-sBST2-GST were obtained by SDS/PAGE electrophoresis.

EXAMPLE 6

Preparation of Human Antibody-Producing Mouse

The mouse used for immunization was genetically homozygous for endogenous Ig heavy chain breakdown and κ light chain breakdown, and simultaneously retained a chromosome 14 fragment (SC 20) containing a human Ig heavy chain locus and a human Igκ chain transgene (KCo5). This mouse was prepared by mating a mouse having a human Ig heavy chain locus (lineage A) with a mouse having a human Igκ chain transgene (lineage B). Lineage A is homozygous for both endogenous Ig heavy chain and κ light chain breakdown, and retains a chromosome 14 fragment (SC20) that is transmittable. For example, it is described in the report by Tomizuka et al. (Tomizuka. et al., Proc. Natl. Acad. Sci. USA, 2000, Vol. 97: 722). Lineage B is homozygous for both endogenous Ig heavy chain and κ light chain breakdown, and retains a human Igκ chain transgene (KCo5). For example, it is described in the report by Fishwild et al., (Nat. Biotechnol., 1996, Vol. 14: 845). An individual obtained by mating a male mouse of lineage A with a female mouse of lineage B or a female mouse of lineage A with a male mouse of lineage B in which the human Ig heavy chain and the κ light chain can be simultaneously detected in the serum (Ishida & Lonberg, IBC's 11th Antibody Engineering, Abstract 2000) was used in the following immunity experiment. The aforementioned human antibody-producing mouse can be obtained from Kirin Brewery Co., Ltd. by making a contract.

EXAMPLE 7

Preparation of Human Monoclonal Antibody Against Human BST2

In this example, a monoclonal antibody was prepared in accordance with a common technique as described in, for example, "*Tan-kuron koutai jikken sousa nyuumon* (A guide to monoclonal antibody experiments)" (Tamie ANDO et al., Kodansha Ltd. Publishers, 1991). The pTracer-CMV/hBST2 vector prepared in Example 1 and the FLAG-sBST2 prepared in Example 5 were used as the immunogen human BST2. A human antibody-producing mouse prepared in Example 6 was used as an animal to be immunized.

The human antibody-producing mouse was subjected to first immunization by introducing and expressing the pTracer-CMV/hBST2 vector (10 µg/mouse) prepared in Example 1 using a reagent for TRANS IT™ In Vivo Gene Delivery System (Takara Shuzo Co., Ltd.). After the first immunization, the same vector was introduced and expressed three times every week for additional immunization. Further, additional immunization was carried out by the tail vein injection of 10 µg of FLAG-sBST2 prepared in Example 5, and the mouse was similarly immunized with 10 µg of FLAG-sBST2 three days before obtaining the spleen cell described below.

The spleen was surgically obtained from the immunized mouse, the recovered spleen cell and mouse myeloma SP2/0 (ATCC No.: CRL1581) were mixed with each other at a ratio of 5:1. Cell fusion was performed using polyethylene glycol 1500 (Boehringer Mannheim) as a fusing agent to prepare a large number of hybridomas. A hybridoma was selected by culturing it in an HAT-containing DMEM medium (Gibco BRL) containing 10% fetal calf serum (FCS), hypoxanthine (H), aminopterin (A), and thymidine (T). Further, a single clone was obtained by limiting dilution using an HT-containing DMEM medium. Culture was conducted in a 96-well microtiter plate (Becton Dickinson). The selection of a hybridoma clone that produces the anti-human hBST2 human monoclonal antibody (screening) and the characterization of the human monoclonal antibody that is produced by each hybridoma were carried out with enzyme-linked immunosorbent assay (ELISA) and a fluorescence activated cell sorter (FACS) as described later.

In the screening of human monoclonal antibody-producing hybridomas by ELISA, many hybridomas were obtained, which produced human monoclonal antibodies having human immunoglobulin γ chain (hIgγ) and human immunoglobulin light chain κ, and which had specific reactivity to human hBST2, based on three types of ELISA and FACS analysis as described later. In the table and drawings in the following examples, including this example, and test results in the examples, a hybridoma clone that produces the human anti-human hBST2 monoclonal antibody according to the present invention was represented by a symbol. The following hybridoma clone indicates a single clone: 2-1L, 2-20J, 5-7I, 5-85H, 7-90G, 8-19O, b-76-8, or 9-16-1.

Four hybridoma clones thereof, i.e., 5-7I, 7-90G, 9-16-1, and b-76-8, were deposited internationally under the Budapest Treaty at the International Patent Organism Depositary of the National Institute of Advanced Industrial Science and Technology (Tsukuba Central 6, 1-1-1 Higashi, Tsukuba, Ibaraki, Japan). Hybridoma clones 5-7I and 7-90G were under accession numbers of FERM BP-7417 and FERM BP-7418 (as of Dec. 26, 2000) and hybridoma clones 9-16-I and b-76-8 are under accession numbers of FERM BP-7821 and FERM BP-7822 (as of Dec. 7, 2001).

EXAMPLE 8

Detection of Monoclonal Antibody Having Human Immunoglobulin γ Chain

The FLAG-sBST2-GST (1 µg/ml 50 mM $Na_2HCO_3$, 50 µl/well) prepared in Example 5 was added to each well of the 96-well microplate for ELISA (Maxisorp, Nunc), incubation was carried out at room temperature for 30 minutes, and the FLAG-sBST2-GST was allowed to adsorb on the microplate. Subsequently, the supernatant was discarded, a blocking reagent (SUPERBLOCK™, Blocking Buffer, PIERCE) was added to each well, incubation was carried out at room temperature for 10 minutes, and a site where FLAG-sBST2-GST was not bound was blocked. Thus, a microplate, each well of which has been coated with FLAG-sBST2-GST, was prepared.

A culture supernatant (50 µl) of each hybridoma was added to each well, the reaction was allowed to proceed at room temperature for 30 minutes, and each well was then washed twice with a 0.1% Tween 20-containing phosphate buffer (PBS-T). Subsequently, a peroxidase-labeled goat anti-human IgGF(ab')$_2$ antibody (Biosource International) was diluted 2000-fold using PBS-T containing 10% Block Ace (Dainippon Pharmaceutical Co., Ltd.) to prepare a solution. The prepared solution was added to each well (50 µl/well) and incubated at room temperature for 30 minutes. The microplate was washed three times with PBS-T, a chromogenic substrate solution (TMB, DAKO) was added to each well (100 µl/well), and incubation was carried out at room temperature for 20 minutes. 2M sulfuric acid was added to each well (50 µl/well) to terminate the reaction. The absorbance at 450 nm (reference wavelength: 570 nm) was assayed using a microplate reader (MTP-300, Corona Electric Co., Ltd.). As a result, 300 or more clones of anti-human BST2 antibodies were obtained. A part thereof is shown in Table 1.

EXAMPLE 9

Detection of Monoclonal Antibody Having Human Immunoglobulin Light Chain κ (IgLκ)

The FLAG-sBST2-GST (1 µg/ml 50 mM $Na_2HCO_3$, 50 µl/well) prepared in Example 5 was added to each well of the 96-well microplate for ELISA (Maxisorp, Nunc), incubation was carried out at room temperature for 30 minutes, and the FLAG-sBST2-GST was allowed to adsorb on the microplate. Subsequently, the supernatant was discarded, a blocking reagent (SUPERBLOCK™, Blocking Buffer, PIERCE) was added to each well, and incubation was carried out at room temperature for 10 minutes. Each well was washed twice with PBS-T. A culture supernatant (50 µl) of each hybridoma was added to each well of the FLAG-sBST2-GST-coated microplate, and the reaction was allowed to proceed for 30 minutes. Thereafter, each well was washed twice with PBS-T. Subsequently, a peroxidase-labeled goat anti-human Igκ antibody (diluted 2000-fold, Biosource International) was added to each well (50 µl/well), and incubation was carried out at room temperature for 30 minutes. After washing three times with PBS-T, a substrate buffer (TMB, DAKO) was added to each well (100 µl/well), and incubation was carried out at room temperature for 20 minutes. 2M sulfuric acid (50 µl) was then added to each well to terminate the reaction. The absorbance at 450 nm (reference wavelength: 570 nm) was assayed using a microplate reader (MTP-300, Corona Electric Co., Ltd.). The results are shown in Table 1.

TABLE 1

| Clone | Subclass | FLAG-sBST2-GST ELISA ($A_{450\,nm}/A_{570\,nm}$) |
|---|---|---|
| 2-1L | IgG4 (κ) | 0.649 |
| 2-20J | IgG1 (κ) | 0.637 |
| 5-7I | IgG1 (κ) | 0.536 |
| 5-85H | IgG1 (κ) | 0.552 |
| 6-26H | IgG4 (κ) | 1.040 |
| 7-90G | IgG1 (κ) | 0.325 |
| 8-19O | IgG1 (κ) | 0.515 |

TABLE 1-continued

| Clone | Subclass | FLAG-sBST2-GST ELISA ($A_{450\,nm}/A_{570\,nm}$) |
|---|---|---|
| b-76-8 | IgG1 (κ) | 0.823 |
| 9-16-1 | IgG4 (κ) | 0.741 |
| Control | IgG1 (κ) | 0.014 |
| Control | IgG4 (κ) | 0.013 |

EXAMPLE 10

Subclass Identification of Each Monoclonal Antibody

The FLAG-sBST2-GST (1 μg/ml 50 mM $Na_2HCO_3$) prepared in Example 5 was added to each well (50 μl/well) of the 96-well microplate for ELISA (Maxisorp, Nunc), incubation was carried out at room temperature for 30 minutes, and the FLAG-sBST2-GST was allowed to adsorb on the microplate. Subsequently, the supernatant was discarded, a blocking reagent (SUPERBLOCK™, Blocking Buffer, PIERCE) was added to each well, and incubation was carried out at room temperature for 10 minutes. Each well was washed twice with PBS-T. A culture supernatant (50 μl) of each hybridoma was added to each well of the FLAG-sBST2-GST-coated microplate, and the reaction was allowed to proceed for 30 minutes. Thereafter, each well was washed twice with PBS-T. Subsequently, a peroxidase-labeled sheep anti-human IgG1 antibody, sheep anti-human IgG2 antibody, sheep anti-human IgG3 antibody, or sheep anti-human IgG4 antibody (diluted 2000-fold, Binding Site) was added to each well (50 μl/well), and incubation was carried out at room temperature for 30 minutes. After washing three times with PBS-T, a substrate buffer (TMB, DAKO) was added to each well (100 μl/well), and incubation was carried out at room temperature for 20 minutes. 2M sulfuric acid (50 μl) was then added to each well to terminate the reaction. The absorbance at 450 nm (reference wavelength: 570 nm) was assayed using a microplate reader (MTP-300, Corona Electric Co., Ltd.). The results are shown in Table 1.

EXAMPLE 11

Reaction Test of Each Monoclonal Antibody Against hBST2 Expression Cell Line

Reactivity of each monoclonal antibody against the myeloma-derived cell strain RPMI 8226 (ATCC CCL-155, Goto et al., Blood, 1994, Vol. 84: 1992: Ohtomo et al., Biochem Biophys Res Commu., 1999, Vol. 258: 583) that has been reported to express BST2 therein was analyzed by FACS. The RPMI 8226 cell line was suspended in a Staining Buffer (SB) of PBS containing 1% rabbit serum, 0.1% $NaN_3$, and 2% FCS at a concentration of $2\times10^6$/ml. A cell suspension (100 μl/well) was fractionated in a 96-well, round bottom plate (Becton Dickinson). A culture supernatant (50 μl) of each hybridoma was added and incubated on ice for 30 minutes. The human IgG1 antibody (SIGMA) or human IgG4 antibody (SIGMA) was used as a negative control depending on each subclass, adjusted to 2 μg/ml in a hybridoma culture medium, and 50 μl thereof was added to perform incubation on ice for 30 minutes. After washing twice with SB, 30 μl of 0.0125 mg/ml RPE fluorescence-labeled rabbit anti-human IgLκF(ab')$_2$ antibody (DAKO) was added, and incubation was carried out under ice cooling for 30 minutes. After washing twice with SB, the resultant was suspended in 300 μl of FACS buffer, and the average fluorescence intensity of each cell was measured by FACS (FACScan, Becton Dickinson). As a result, all the antibodies were found to have strong binding activities against the RPMI 8226 cell line (FIG. 1).

EXAMPLE 12

Preparation of Each Antibody

A culture supernatant containing an anti-BST2 antibody was prepared in the following manner. The anti-BST2 antibody-producing hybridoma was adapted to eRDF medium (Kyokuto Seiyaku) containing bovine insulin (5 μg/ml, Gibco BRL), human transferin (5 μg/ml, Gibco BRL), ethanolamine (0.01 mM, SIGMA), and sodium selenite ($2.5\times10^{-5}$ mM, SIGMA). Culture was conducted in a spinner flask, and the culture supernatant was collected when the rate of surviving hybridomas reached 90%. The collected supernatant was applied to 10 μm- and 0.2 μm-filters (Gelman Science) to eliminate waste such as hybridomas.

The anti-BST2 antibody was purified from the culture supernatant in the following manner. The culture supernatant containing the anti-BST2 antibody was subjected to affinity purification using the Hyper D Protein A Column (NGK Insulators, LTD.) in accordance with the attached instructions. PBS(−) was used as an adsorption buffer, and 0.1M sodium citrate buffer (pH 3) was used as an elution buffer. An elution fraction was adjusted to around pH 7.2 with the addition of 1M Tris-HCl (pH 8.0). The prepared antibody solution was converted into PBS(−) using a dialysis membrane (molecular weight cut off: 10,000, Spectrum Laboratories) and filter-sterilized with a membrane filter MILLEX-GV (pore diameter: 0.22 μm, MILLIPORE) to obtain a purified anti-BST2 antibody. The absorbance at 280 nm was assayed, and 1 mg/ml was set to be 1.45 OD to determine the concentration of the purified antibody.

EXAMPLE 13

Fluorescence Labeling of Anti-BST2 Antibody

The anti-BST2 antibody was subjected to fluorescence labeling in the following manner. ALEXA FLUOR™ 488 (Molecular Probes) was bound to the anti-BST2 antibody prepared in Example 12 in accordance with the attached instructions. A 1M carbonate buffer (50 μl) was added to 0.5 ml of 2 mg/ml anti-BST2 antibody, the resultant was mixed with ALEXA FLUOR™ 488, and the reaction was allowed to proceed at room temperature for 1 hour while stirring. Hydroxylamine was added to terminate the reaction, the mixed solution was applied to a gel filtration column (NAP5, Amersham Pharmacia Biotech), and ALEXA FLUOR™ which is not bound to the antibody was removed. Under this condition, six fluorescent substances were bound to one antibody molecule. The fluorescence-labeled antibody was bound to RPMI 8226, and its binding activity was equivalent to that of the unlabeled antibody.

EXAMPLE 14

Cross-Reactivity of Each Anti-BST2 Antibody

Cross-reactivity of each monoclonal antibody with blood cells of a mouse and a Rhesus monkey was investigated by FACS. Human peripheral blood (10 mL) or 10 mL of Rhesus monkey peripheral blood containing 1 mL of heparin (Novo) was diluted twofold with the aid of 10 mL of PBS(−) and superposed in 20 mL of Ficoll-Paque PLUS solution (Amersham Pharmacia Biotech). After being centrifuged at 1,500 rpm for 30 minutes, a mononuclear fraction was collected and washed twice with PBS(−). The mouse blood cells were prepared in the following manner. Peripheral blood (50 μL) was sampled by orbital sinus blood sampling in an EDTA-coated test tube. After the addition of 300 μL of sterilized water, 300 μL of 2×PBS(−) was immediately added, and the resultant was washed twice with PBS(−). Each of the prepared cells was suspended in the Staining Buffer (SB) of PBS containing 1% human serum, 0.1% $NaN_3$, and 2% FCS at a concentration of $2 \times 10^6$/ml. A cell suspension (100 μl/well) was fractionated in a 96-well, round bottom plate (Becton Dickinson). Each Alexa-labeled antibody prepared in Example 13 was incubated at 5 μg/mL under ice cooling for 30 minutes. After washing twice with SB, the incubation product was suspended in 300 μl of FACS buffer, and the reactivity of each antibody was investigated by FACS (FACScan, Becton Dickinson). As a result, all the antibodies bound to human peripheral blood cells, although they did not react with mouse peripheral blood cells. In contrast, b-76-8 and 9-16-1 similarly bound to the Rhesus monkey peripheral blood cells as well as the human peripheral blood cells.

EXAMPLE 15

Evaluation of Activity to Induce BST2 Internalization

Figure 2:
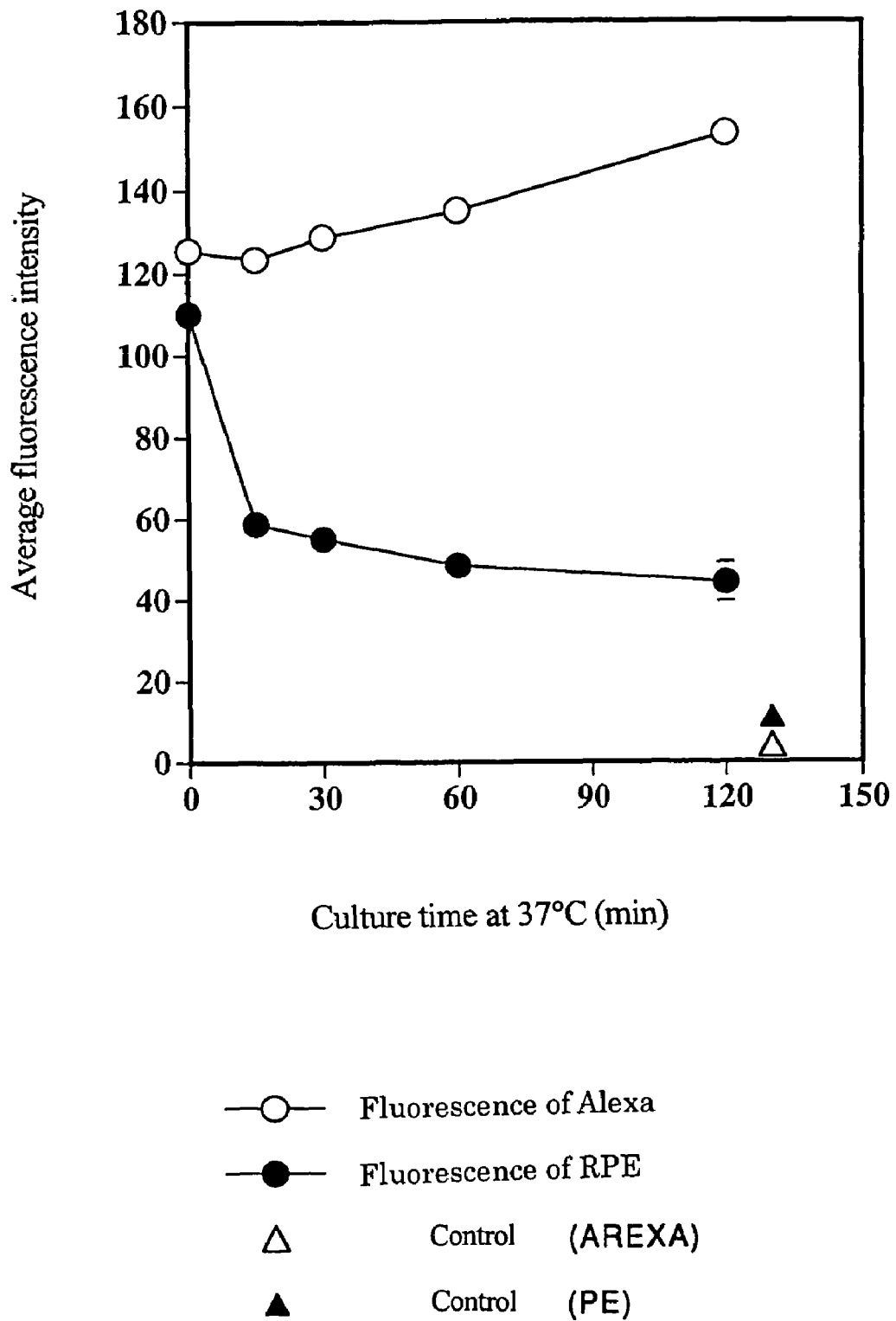
FIG. 2 is a diagram showing activity of an anti-human BST2 antibody (7-90G) to induce internalization.
Figure 3:
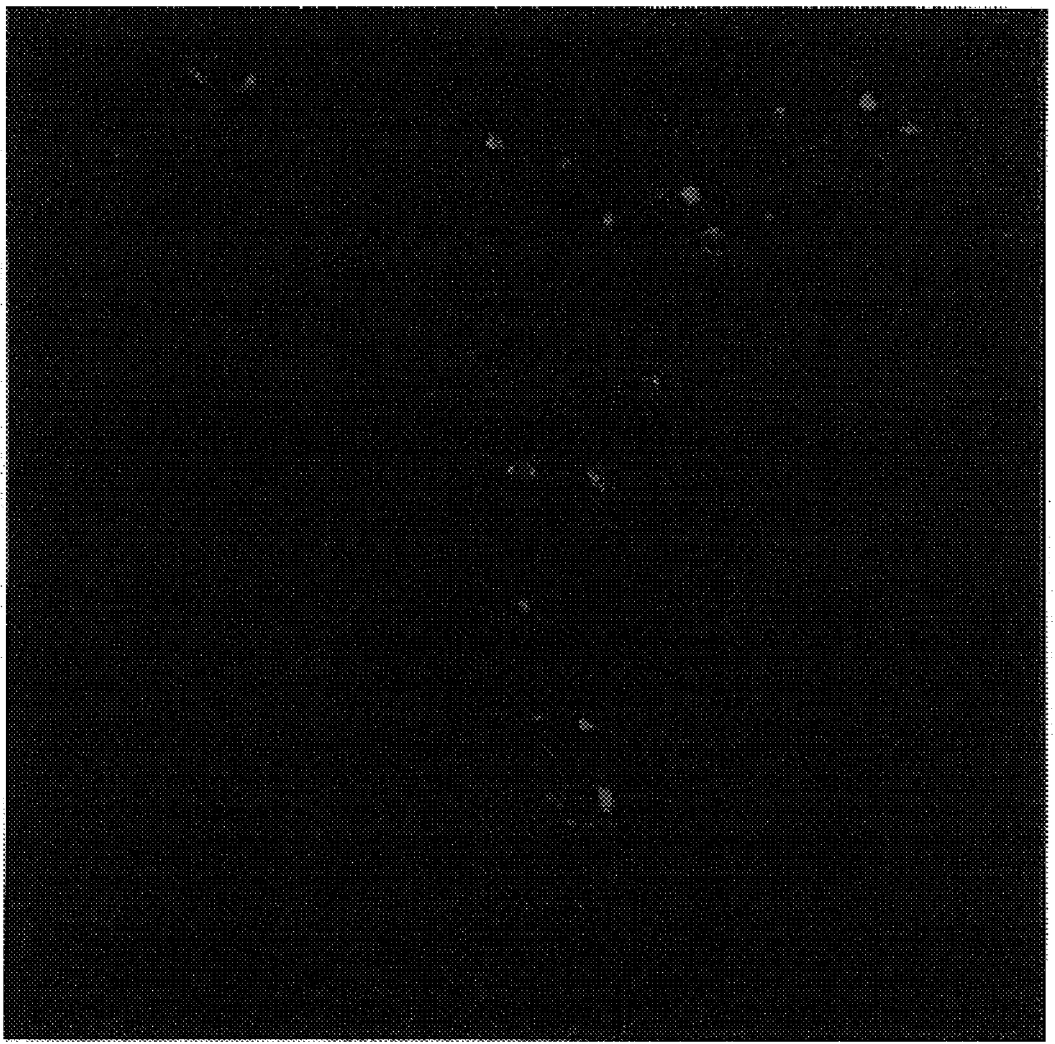
FIG. 3 is a photomicrograph showing an anti-BST2 antibody that is internalized in the RPMI 8226 cell 15 minutes after being cultured at 37° C.

Activity of an antibody to induce antigen internalization was evaluated in accordance with the process according to Andrzej et al. (J. Immunol. 2000, Vol. 165: 6037) in the following manner. The RPMI 8226 strain was suspended in the ice-cooled RPMI medium containing 10% fetal calf serum (FCS) and 1% rabbit serum at a concentration of $2 \times 10^6$/ml, and a cell suspension (100 μl/well) was fractionated in a 96-well, round bottom plate (Becton Dickinson). The ALEXA FLUOR™ 488-labeled anti-BST2 antibody prepared in Example 13 was adjusted to 700 ng/ml in the ice-cooled RPMI medium containing 10% FCS (Gibco BRL), 100 μl thereof was fractionated in each well, and the reaction was allowed to proceed on ice for 30 minutes. By washing four times in the ice-cooled RPMI medium containing 10% FCS, unbound ALEXA FLUOR™ 488-labeled anti-BST2 antibodies were removed from the cells. These cells were resuspended in the 10% FCS-containing RPMI medium, which was heated to 37° C., cultured at 37° C., and washed twice with ice-cooled SB 0, 15, 30, 60, and 120 minutes after the culture in order to terminate internalization. In order to detect an antibody bound to hBST2 on the cell surface, 30 μl of 0.0125 mg/ml RPE fluorescence-labeled rabbit anti-human IgLκF(ab')$_2$ antibody (DAKO) was added, and incubation was carried out under ice cooling for 30 minutes. After washing twice with SB, the cells were suspended in 300 μl of FACS buffer, and the average fluorescence intensity of each cell was assayed by FACScan (Becton Dickinson). In the setting of the background level, sensitivity was suitably set with the use of the ALEXA FLUOR™ 488-labeled isotype control IgG1κ antibody and the RPMI 8226 line in order to bring the average fluorescence intensity, at the initiation of culture at 37° C., of the Alexa sample to between 3 and 5 and that of the RPE sample to between 6 and 8, which have been treated in the aforementioned manner. The results are shown in FIG. 2. The average fluorescence intensity of ALEXA FLUOR™ 488 was not lowered even though it was cultured at 37° C. The average fluorescence intensity of the RPE fluorescent substance representing the amount of an immune complex of BST2/anti-BST2 antibody existing on the cell surface was lowered with the elapse of culture time at 37° C. The average fluorescence intensity of the RPE fluorescent substance was lowered to 50% or below after being cultured for 15 minutes. Accordingly, the anti-BST2 antibody (7-90G) was found to efficiently induce BST2 internalization. Also, conditions of internalization were observed by the fluorescent microscopic examination (FIG. 3). Capping was observed 15 minutes after the initiation of internalization, and the RPE fluorescent substance was observed only through staining on the cell surface. In contrast, the ALEXA FLUOR™ 488 fluorescent substance was found to be internalized in a region adjacent to the cytoplasmic membrane as well as on the cell surface. Fine dots scattered in the membrane were also present in the granules that were supposed to be the Golgi apparatus based on the location. The aforementioned features strongly indicate that, even though the antibody is labeled with a therapeutic agent or the like, the therapeutic agent is highly likely to be effectively exposed in the cell without deterioration of the ability to internalize BST2 in the cell. Equivalent activity was observed also in other anti-BST2 antibodies.

EXAMPLE 16

Preparation of Thiol Group-Introduced Maytansine

In this example, a thiol group was introduced in maytansine with reference to the process according to Chari et al. (Cancer Res., 1992, Vol. 52: 127) or the process as described in U.S. Pat. No. 5,208,020.

Specifically, 20 mg of ansamitocin P-3 (Wako Pure Chemicals Industries, Ltd.) was dissolved in 4 ml of THF, and the solution was reduced with the aid of 33 mg of lithium aluminum hydride (10 equivalent amounts) for 5 hours while cooling to −23° C. The reaction solution was dissolved in 20 ml of 10 mM phosphate buffer (pH 6.5), and extraction was then carried out twice with an equivalent amount of ethyl acetate. The ethyl acetate layer was concentrated to dryness and then purified with a silica gel column ($CH_2Cl_2$:MeOH=20:1), thereby preparing 11.8 mg of maytansinol.

Figure 6:
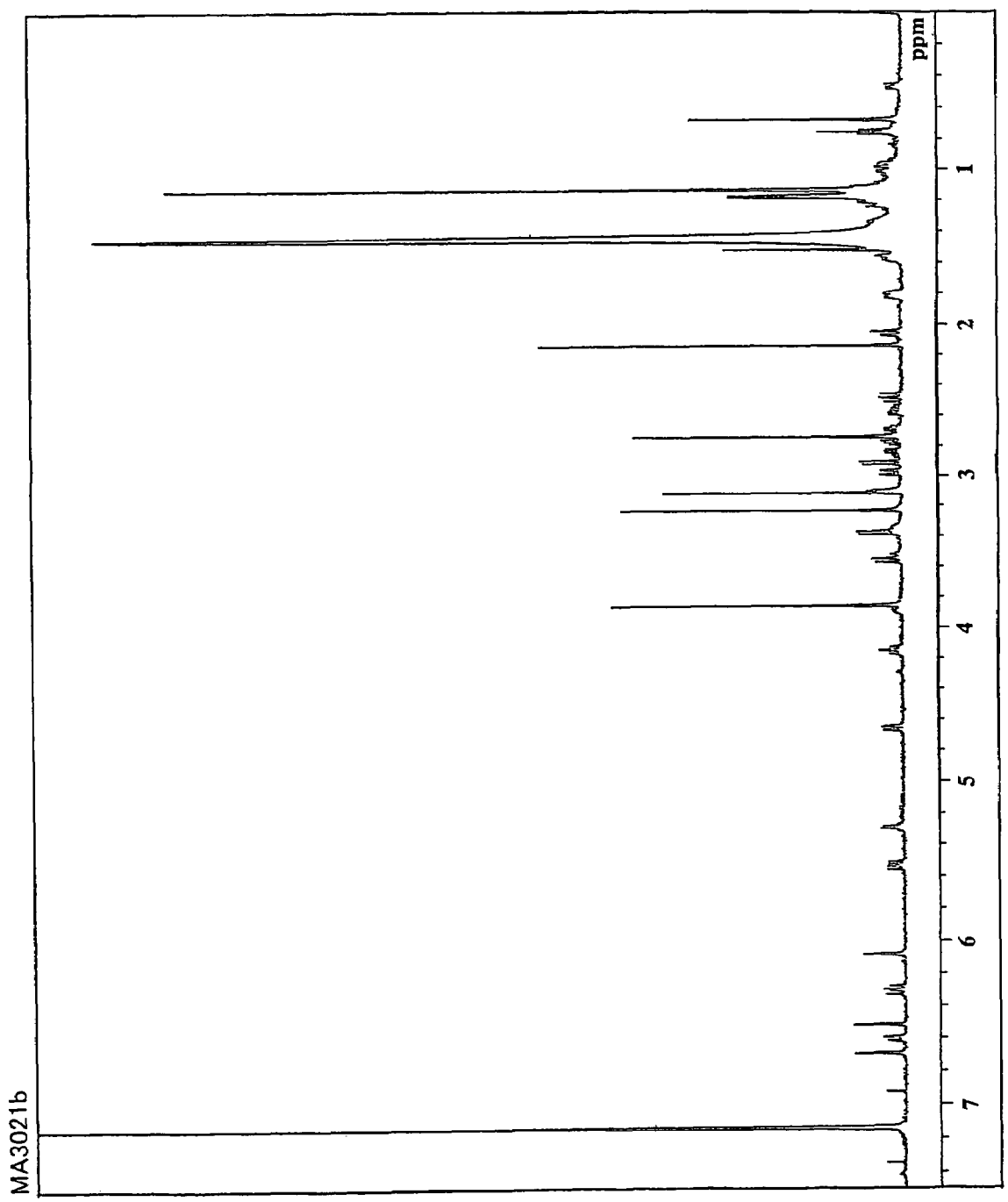
FIG. 6 is a diagram showing the 500 MHz 1H NMR of synthesized maytansine compound.

N-methyl-N-(methyl dithiopropanoyl)-L-alanine (26 mg) prepared by a different process in accordance with a reference was dissolved in 3 ml of $CH_2Cl_2$, 30 mg of dicyclohexylcarbodiimide (2 equivalent amounts) and 20 μl of 1M zinc chloride (1 equivalent amount) were added thereto, and the mixture was stirred at room temperature for 30 minutes. Since the reaction did not proceed under this condition, the amount of 1M zinc chloride added was changed to 100 μl (5 equivalent amounts), and the mixture was stirred at room temperature for 30 minutes. A solution of 11.8 mg of maytansinol in 1 ml of $CH_2Cl_2$ was added thereto for esterification. The reaction solution was concentrated to dryness 3 hours later, the main product was purified by preparative TLC ($CH_2Cl_2$:MeOH=10:1) and then by preparative HPLC (ODS column, eluent: 60% $CH_3CN$). As a result, 2.5 mg of maytansine derivative (May-SS-Me) was obtained. FIG. 6 shows the resulting May-SS-Me by 500 MHz 1H NMR. In the test for assaying the cellular cytotoxicity of the human myeloma cell strain IM9 as described in Example 19, $IC_{50}$ of the obtained May-SS-Me was 10 nM, which was 1/1000 or less than that of ansamitocin P-3.

The resulting May-SS-Me (2.5 mg) was dissolved in a solution comprising 0.46 ml of ethanol and 0.32 ml of 0.1M phosphate buffer (pH 7.5, containing 1 mM EDTA), 80 μl (1.5 equivalent amount) of 100 mM dithiothreitol was added thereto, and the resultant was reduced in the presence of nitrogen gas at 4° C. for 4 hours. The thus obtained reduced compound (May-SH) was purified by the ODS column that was equilibrated with 60% acetonitrile (final yield: 2.0 mg).

EXAMPLE 17

Introducing PDP Group into Anti-BST2 Antibody (b-76-8)

In this example, a thiol group was introduced in an antibody with reference to the process according to Chari et al. (Cancer Res., 1992, Vol. 52: 127) and the process as described in *Shin-seikagaku jikken kouza; Bunshi menekigaku* (New Biochemical Experiment: Molecular Immunology) III (the Japanese Biochemical Society (ed), Tokyo Kagaku Dojin Co., Ltd., 1992) using N-succinimidyl-3-(2-pyridyldithio) propionate (SPDP, PIERCE). The purified antibody b-76-8 was adjusted to 2.6 mg/mL with the aid of a 0.1M sodium phosphate buffer (pH 7.5) containing 0.1M NaCl. A solution of 11.5 mM SPDP-ethanol (42.3 μl) was added dropwise to 5 ml of 2.6 mg/ml antibody solution, and the reaction was allowed to proceed at 23° C. for 40 minutes. The reaction solution was applied to the SEPHADEX™ G-25 Column (NAP25™, Amersham Pharmacia Biotech), which was equilibrated with 2 mM EDTA-containing 0.1M potassium phosphate buffer (pH 7.0) to remove unreacted SPDP. Dithiothreitol was added to a part of the obtained sample to a concentration of 1 mM, and the mixture was allowed to react at room temperature for 5 minutes. After the reaction, the absorbance of free pyridine-2-thione at 343 nm was assayed, and the molarity of the PDP group existing in the reaction system was quantified ($\epsilon$ of pyridine-2-thione=$8.08 \times 10^3$). As a result, the introduced PDP group had a ratio of 3.4 molecules per antibody.

EXAMPLE 18

Preparation of Maytansine-b-76-8 Antibody Conjugate

The May-SH prepared in Example 16 (170 μg/800 μl) and the PDP group introduced b 76-8 prepared in Example 17 (10 mg/9 mL) were allowed to react at 4° C. for 40 hours. The reaction solution was applied to the SEPHADEX™ G-25 column that was equilibrated with a phosphate buffer (pH 7.4) to remove unreacted May-SH. Dithiothreitol was added to a part of the obtained sample to a concentration of 1 mM, and the mixture was allowed to react at room temperature for 5 minutes. After the reaction, the absorbance of free pyridine-2-thione at 343 nm was assayed, and the molarity of the PDP group existing in the reaction system was quantified. As a result, the introduced maytansine compound had a ratio of 1.8 molecules per antibody. Cysteine was added to a concentration of 0.1M, and the reaction solution was applied to the SEPHADEX™ G-25 column that was equilibrated with a phosphate buffer (pH 7.4) to purify a maytansine-b-76-8 antibody conjugate (May-b-76-8).

EXAMPLE 19

Antitumor Activity of Maytansine-b-76-8 Antibody Conjugate

In the same manner as in Example 11, the reactivity to the human myeloma cell line IM9 cell (ATCC CCL-159) was investigated. As a result, the May-b-76-8 antibody exhibited reactivity equivalent to that of the b-76-8 antibody. The antitumor activity of the May-b-76-8 antibody was investigated as follows. The $2 \times 10^5$/ml IM9 cells(100 μl), the b-76-8 antibody, the May-b-76-8 antibody, or a control human IgG1 was added to each well of a 96-well, round bottom plate (Becton Dickinson), and culture was conducted in a $CO_2$-incubator for 24 hours. Thereafter, a solution of MTS (3-(4,5-dimethylthiazol-2-yl)-5-(3-carboxymethoxyphenyl)-2-(4-sulphophenyl)-2H-tetrazolium, Promega) was added to each well in amounts of 20 μl each, followed by culturing for an additional 2 hours. Subsequently, the absorbance at 490 nm of the surviving cells was assayed using a microplate reader (MTP-300, Corona Electric Co., Ltd.). As a result, when the control human IgG1 and the b-76-8 antibody were added to the IM9 cells, no significant cell damaging activity was observed. In the case of the May-b-76-8 antibody, cellular cytotoxicity was observed depending on its concentration, and $IC_{50}$ was 10 nM (maytansine concentration)/5.5 nM (antibody concentration).

EXAMPLE 20

Antitumor Effect of Maytansine-b-76-8 Antibody Conjugate on a Model Mouse for Human Myeloma The antibody to be administered was prepared using filter-sterilized PBS(−) to a concentration of 800 μg/ml.

Human myeloma-transplanted mice were prepared as follows. The human myeloma cell line IM9 cells were transplanted to the SCID mice (CLEA Japan, Inc.) to a concentration of $2.5 \times 10^7$/ml with the aid of PBS(−). The aforementioned IM9 cell solution (200 μl) was injected through the tail veins of the SCID mice (female, 6-week-old, CLEA Japan, Inc.) that had been subjected to the tail vein injection with 100 μl of anti-asialo GM1 (Wako Pure Chemicals Industry, Ltd.) on the previous day. Six to ten days after the IM9 cells inoculation, prepared antibodies were intravenously administered to these mice on successive days in amounts of 200 μl each.

Figure 7:
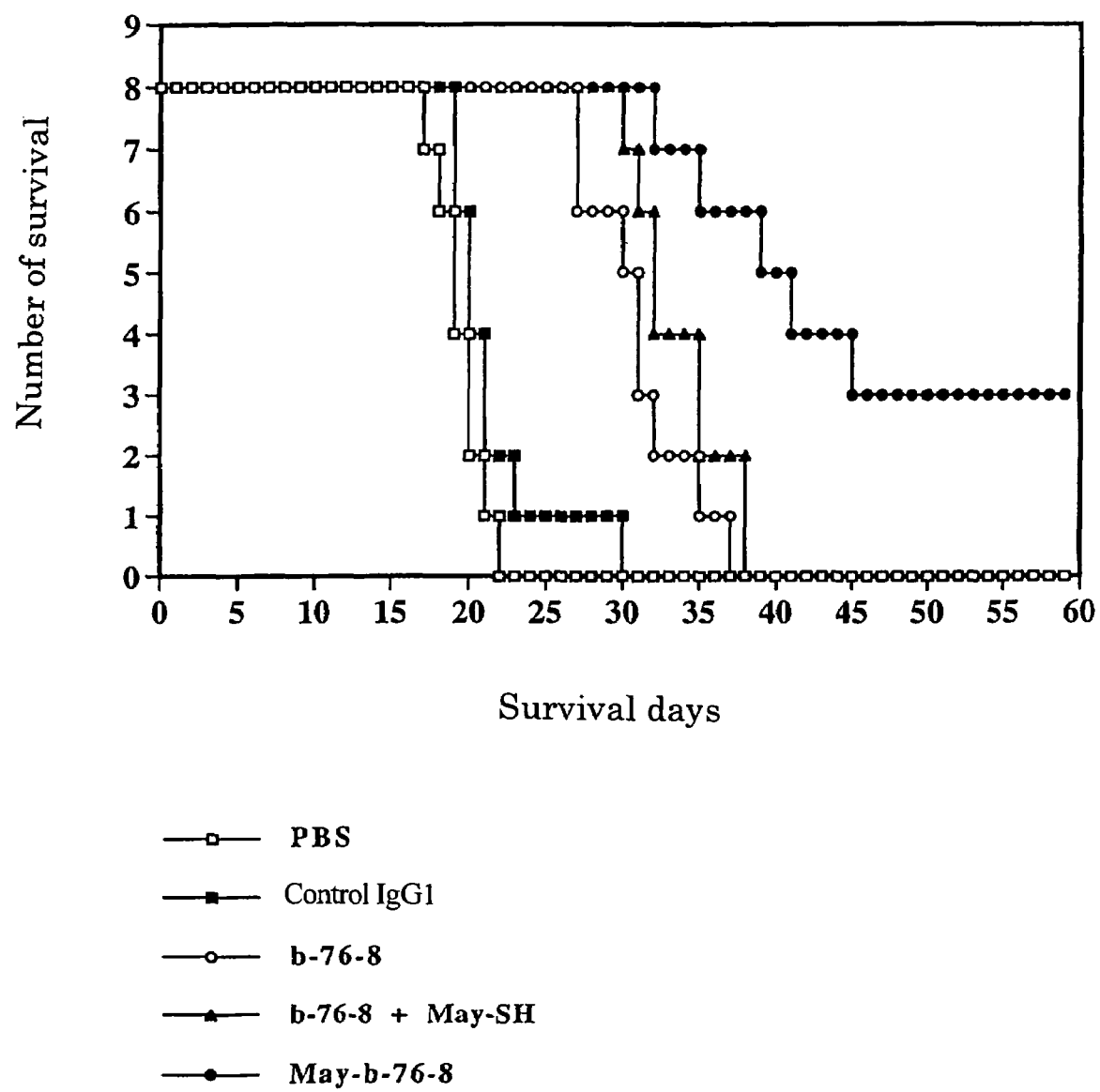
FIG. 7 is a diagram showing anti-tumor effects of the maytansine-b-76-8 antibody conjugate on mouse model of human myeloma.

The anti-tumor effect of the May-b-76-8 antibody was evaluated based on the survival times of mice. As a result, as shown in FIG. 7, death was observed approximately twenty days after the IM9 cell inoculation in the control group administered with PBS(−) and in the isotype control group administered with human IgG1. In the group administered with PBS(−), all mice deceased twenty two days after the inoculation, and similar survival times were observed in the isotype control group administered with human IgG1. Compared with the control groups, the survival time of the group administered with the b-76-8 antibody was prolonged (p<0.01, Logrank test). Further, compared to the group administered with the b-76-9-8 antibody, the survival time of the group administered with the May-b-76-8 antibody was significantly prolonged (p<0.05). In contrast, simultaneous administration of the b-76-8 antibody and the May-SH (1.9 nmol/shot) did not result in significant prolongation in survival time compared with the group administered with b-76-8 (p>0.1). These results indicate that the May-b-76-8 antibody had antitumor effects on human myeloma xenografts in mice and the antitumor effects of this antibody are stronger than that obtained by sole administration of the b-76-9-8 antibody. This indicates that more potent antitumor effects can be expected by binding a substance having antitumor activity such as a maytansinoid compound to the anti-BST2 antibody that can be internalized. Accordingly, this antibody can be an innovative therapeutic agent for myeloma.

This description includes part or all of the content as disclosed in the description and/or drawings of Japanese Patent Application No. 2000-403245, which is a priority document of the present application. All publications, patents, and patent applications cited herein are incorporated herein by reference in their entirety.

FREE TEXTS OF SEQUENCE LISTINGS

SEQ ID NO: 3: description of an artificial sequence: primer

SEQ ID NO: 4: description of an artificial sequence: primer

SEQ ID NO: 5: description of an artificial sequence: primer

SEQ ID NO: 6: description of an artificial sequence: primer

SEQ ID NO: 7: description of an artificial sequence: primer

SEQ ID NO: 8: description of an artificial sequence: primer

SEQ ID NO: 9: description of an artificial sequence: primer

INDUSTRIAL APPLICABILITY

The monoclonal antibody according to the present invention binds to a human BST2 antigen on the cell surface and can be localized through internalization into the cell. Accordingly, a therapeutically useful agent that was bound to this antibody can be effectively transmitted in cells such as multiple myeloma cells, lymphoid tumor cells, or primary localized cancer cells that express BST2 on their surfaces. This can provide a therapeutic agent based on a novel mechanism in the treatment of obstinate diseases.

The invention claimed is:

1. A monoclonal antibody produced by a hybridoma under accession number FERM BP-7417, FERM BP-7418, FERM BP-7821, or FERM BP-7822 or a fragment of the antibody, which fragment binds to the same antigen that the full-length antibody binds to, wherein the antibody or the fragment thereof:
   (i) binds to a human BST2 antigen existing on a cell surface, and
   (ii) can be localized through internalization into the cell.

2. A monoclonal antibody or a fragment thereof obtained by
   (A) cloning the human antibody genes or the partial sequences encoding said fragment from a hybridoma under accession number FERM BP-7417, FERM BP-7418, FERM BP-7821, or FERM BP-7822,
   (B) incorporating said genes or said partial sequences into an expression vector,
   (C) introducing said vector into a host cell, and
   (D) culturing the host cell, wherein the antibody or the fragment thereof:
   (i) binds to a human BST2 antigen existing on a cell surface, and
   (ii) can be localized through internalization into the cell having the human BST2 antigen existing on the surface.

3. A complex comprising the monoclonal antibody or the fragment thereof according to claim 1 that is conjugated to an agent selected from the group consisting of a radionuclide, a bacterial toxin, and a chemotherapeutic.

4. The complex according to claim 3, which is a maytansine-antibody conjugate.

* * * * *

UNITED STATES PATENT AND TRADEMARK OFFICE
CERTIFICATE OF CORRECTION

PATENT NO. : 7,592,005 B2  Page 1 of 1
APPLICATION NO. : 10/451947
DATED : September 22, 2009
INVENTOR(S) : Tomoyuki Tahara It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 539 days.

Signed and Sealed this

Twenty-first Day of September, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 552
<212> TYPE: DNA
<213> ORGANISM: Homo sapiens

<400> SEQUENCE: 1
gtggaattca tggcatctac ttcgtatgac tattgcagag tgcccatgga agacggggat      60
aagcgctgta agcttctgct ggggatagga attctggtgc tcctgatcat cgtgattctg     120
ggggtgccct tgattatctt caccatcaag gccaacagcg aggcctgccg ggacggcctt     180
cgggcagtga tggagtgtcg caatgtcacc catctcctgc aacaagagct gaccgaggcc     240
cagaagggct tcaggatgt ggaggcccag ccgccacct gcaaccacac tgtgatggcc       300
ctaatggctt ccctggatgc agagaaggcc caaggacaaa agaaagtgga ggagcttgag     360
ggagagatca ctacattaaa ccataagctt caggacgcgt ctgcagaggt ggagcgactg     420
agaagagaaa accaggtctt aagcgtgaga atcgcggaca agaagtacta ccccagctcc     480
caggactcca gctccgctgc ggcgccccag ctgctgattg tgctgctggg cctcagcgct     540
ctgctgcagt ga                                                         552

<210> SEQ ID NO 2
<211> LENGTH: 180
<212> TYPE: PRT
<213> ORGANISM: Homo sapiens

<400> SEQUENCE: 2

Met Ala Ser Thr Ser Tyr Asp Tyr Cys Arg Val Pro Met Glu Asp Gly
  1               5                  10                  15

Asp Lys Arg Cys Lys Leu Leu Leu Gly Ile Gly Ile Leu Val Leu Leu
                 20                  25                  30

Ile Ile Val Ile Leu Gly Val Pro Leu Ile Ile Phe Thr Ile Lys Ala
             35                  40                  45

Asn Ser Glu Ala Cys Arg Asp Gly Leu Arg Ala Val Met Glu Cys Arg
         50                  55                  60

Asn Val Thr His Leu Leu Gln Gln Glu Leu Thr Glu Ala Gln Lys Gly
     65                  70                  75                  80

Phe Gln Asp Val Glu Ala Gln Ala Ala Thr Cys Asn His Thr Val Met
                 85                  90                  95
```

```
Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 3
aaggaaaaaa gcggccgcgt ggaattcatg gcatctac                          38

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 4
ctagtctaga tcatcactgc agcagagcgc tgagg                             35

<210> SEQ ID NO 5
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agatctatga aattcttagt caacgttgcc cttgttttta tggtcgtata catttcttac   60
atctatgcgg atcgagacta caaggatgac gatgacaagg gatcc                  105

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
cgaggatccc atatgcggga cggccttcgg gc                                32

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 7
```

```
aaggaaaaaa gcggccgctc actgcagcag agcgctgagg                              40

<210> SEQ ID NO 8
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 8
aaggaaaaaa gcggccgcgc tggaagttct gttccagggg cccatgtccc ctatactagg       60
ttattgg                                                                 67

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 9
cggggtacct caatccgatt ttggaggatg gtcgcc                                 36

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: FLAG tag

<400> SEQUENCE: 10

Asp Tyr Lys Asp Asp Asp Asp Lys
 1               5
```